United States Patent [19]

Archerd

[11] 4,060,001
[45] Nov. 29, 1977

[54] SAMPLING PROBE AND METHOD OF USE

[75] Inventor: Paul H. Archerd, Bartlesville, Okla.

[73] Assignee: Phillips Petroleum Company, Bartlesville, Okla.

[21] Appl. No.: 718,302

[22] Filed: Aug. 27, 1976

[51] Int. Cl.² ............................................. G01N 1/24
[52] U.S. Cl. ................................................ 73/421.5 R
[58] Field of Search .................. 73/421 R, 421 A; 239/DIG. 7

[56] References Cited
U.S. PATENT DOCUMENTS

| 3,784,902 | 1/1974 | Huber | 73/421.5 |
| 3,795,367 | 3/1974 | Mocarski | 417/197 |
| 3,938,930 | 2/1976 | Grey | 73/421.5 |

FOREIGN PATENT DOCUMENTS 953,926  12/1956  Germany.

Primary Examiner—S. Clement Swisher

[57] ABSTRACT

A sampling probe and method for its use in which a flow amplifier utilizing the Coanda wall attachment effect has attached to its inlet an isokinetic sampling nozzle and has attached to its outlet a straight tube so that upon passing a flow of compressed, motive gas through the throttling inlet of the flow amplifier, a flow of sample gas is induced from a gaseous external environment of the probe and the motive gas provides a barrier between the sample gas and the wall of the flow amplifier and attached tube. In an embodiment of the invention the motive gas is a dry gas at elevated temperature which reduces moisture content of samples of moist gas environments.

9 Claims, 1 Drawing Figure

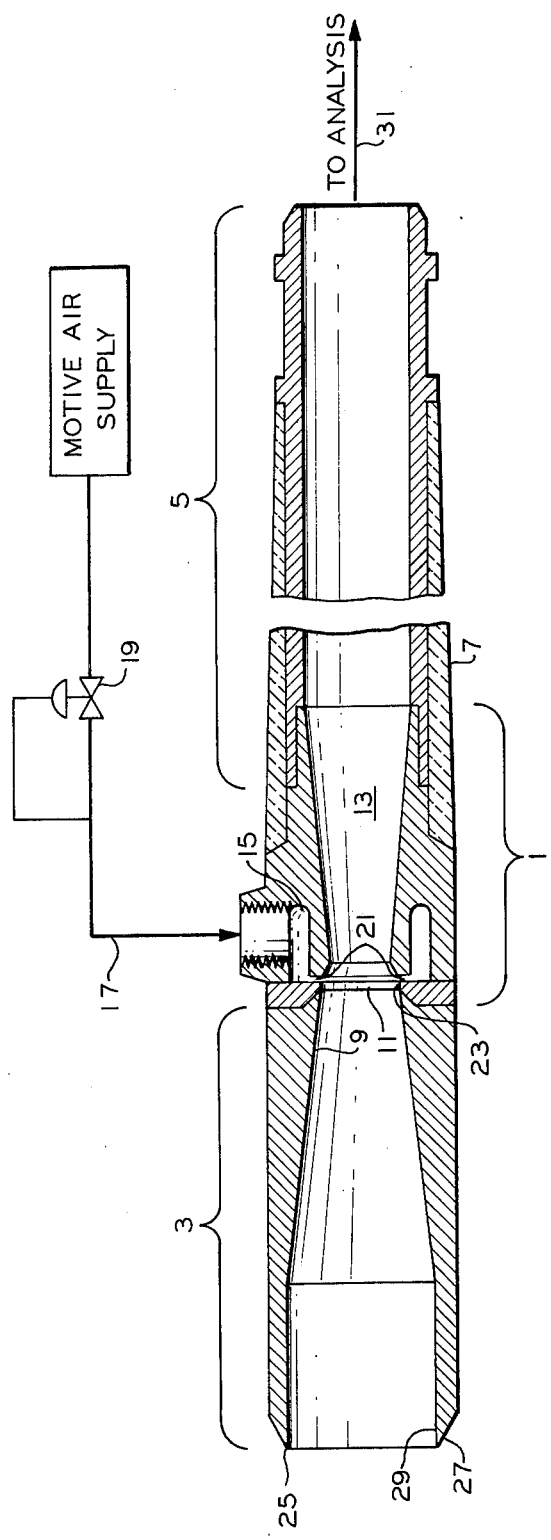

SAMPLING PROBE AND METHOD OF USE

BACKGROUND OF THE INVENTION

This invention relates to sampling apparatus and methods. In one of its aspects this invention relates to inducing flow of gaseous samples from a gaseous environment. In another of its aspects this invention relates to drying moist gaseous samples. In yet another aspect this invention relates to the handling of particulate matter collected from a moist gaseous medium. In yet another aspect of the invention it relates to the prevention of deposition of solid particulate matter on the walls of a sample collection probe.

Sample probes for the collection of gaseous samples or gaseous samples containing particulate matter are well known in the art. It has become common practice to induce a flow into a sample collecting probe from a surrounding gaseous medium by directing motive air flow inside a conduit at a high speed so that air is entrained from the surroundings of this flow and a larger flow of air is caused to occur. Often, in using ejector-type sample induction devices, solids materials from the sampled medium collect on the walls of the induction tube. This collection of solids material on the walls is particularly evident when, as in the sampling of sea spray, the sampled material is moist and the motive air tends to dry the solids material that are deposited on the induction tube walls.

The sampling of sea spray has become important in determining the effectiveness of methods for reducing the amount of salt spray taken into the air inlet of turbine drives of large ships and other large machinery such as operating equipment in offshore and seaside processing facilities. The sampling of sea spray presents a particularly difficult problem because determination of the salt content of the spray depends on obtaining a representative sample of a material, salt, that is generally in solution in the moisture in the spr;ay and from which the moisture content must be reduced sufficiently to provide solid particles for analysis without losing this particulate material by having it stick to the walls of the sample induction tube. The apparatus and method of this invention are most specifically concerned with obtaining representative salt spray samples for analysis of salt content by determining the amount of sodium present.

It has now been found that the sticking of solid particles to the walls of the induction tube can be substantially eliminated by using an air flow amplifier that utilizes the Coanda effect to provide motive gas for sample flow induction. The Coanda effect, named for Henri Coanda who is a developer of devices utilizing the physical principle that bears his name, is that a flowing fluid will attach itself to an adjacent wall and wall then change directions in accordance with the wall's contours. The Coanda effect can be demonstrated both for liquids and gases. By inducing flow into a sample probe by utilizing the Coanda effect in air flow amplification a barrier of motive air travels along the induction tube wall while allowing mixing of the motive gases with the sampled material for reduction of the relative humidity in the sample. The sample is dried while being kept from contacting the walls of the conduit.

It has also been determined that representative samples of salt spray are best obtained using isokinetic sampling techniques so that there is no disturbance of flow of the stream to be sampled at the point of sampling. The velocity of the sample entering the probe must be the same as the velocity of the ambient gaseous environment. Isokinetic sampling is a well-known procedure and has established limits on sample probe inlet design. It is necessary to take a sample through a knife edge on the front end of a probe with the leading edge of the probe sloping away from the knife edge formed by the inner circumference of the probe at an angle of 30° or less.

Since the apparatus and method provided herein will satisfy conditions for obtaining representative samples of solid particulate matter from moist gaseous environments, the method and apparatus are also appropriate for use in obtaining samples of any gaseous environment.

It is therefore an object of this invention to provide apparatus and method for obtaining representative particulate samples from moist, gaseous environments. It is also an object of this invention to obtain representative samples from moist, gaseous environments containing liquid droplets of solutions of crystallizable chemical compounds. It is another object of this invention to provide a sampling probe using motive gas to shield the walls of the probe from contact with the induced sample flow.

Other aspects, objects, and the various advantages of this invention will become apparent upon study of this specification, the drawing, and the appended claims.

STATEMENT OF THE INVENTION

An apparatus for sampling a gaseous environment is provided in which a flow amplifier utilizing the Coanda wall attachment effect has attached to its inlet an isokinetic sampling nozzle and has attached to its outlet a straight tube. In a preferred embodiment of the invention in which a moist, gaseous environment containing droplets of a crystallizable solution of a chemical compound is sampled the straight tube connected to the outlet of the flow amplifier is of a length sufficient to allow intermixing of the motive air and the induced sample flow to reduce the relative humidity of the induced sample flow.

In accordance with this invention a method is also provided for sampling a gaseous environment. In this method a flow of compressed gas is passed through the throttling inlet of a flow amplifier utilizing the Coanda wall attachment effect thereby inducing flow of sample gas from the gaseous environment through an isokinetic nozzle attached to the inlet of the flow amplifier, through the amplifier, and into a conveying means attached to the amplifier outlet. In a preferred embodiment in which a moist, gaseous environment containing droplets of a crystallizable solution of a chemical compound is sampled, the conveying means attached to the amplifier outlet is a straight tube of length sufficient to allow intermixing of the motive gas with the induced sample flow to reduce the relative humidity of the sample flow.

Air flow amplifiers utilizing the Coanda effect are commercially available from such sources as the Vortec Corporation and Nortel Machinery Incorporated. In these commercial apparatuses compressed air is introduced into an annular chamber surrounding a ring nozzle and the gas is throttled through the ring nozzle and is deflected toward the outlet end of the apparatus. The gas attains sonic velocity in the nozzle and forms a thin sheet of high velocity air which is directed along the downstream wall of the nozzle where it collides with still air which causes the motive air to slow down and the air with which it collided to accelerate toward the outlet. Gas is pulled through the inlet side of the nozzle to replace the air being moved along to the outlet and in this manner a flow of gas is induced through the air amplifier nozzle.

The invention can best be understood in conjunction with the drawing which is a cut-away side view of a sample probe of the present invention.

Referring now to the drawing, the cylindrical sample probe of this invention is composed of a flow amplifier 1 utilizing the Coanda wall attachment effect, an isokinetic sampling nozzle 3, and a straight tube 5 connected to the discharge of the flow amplifier 1. In the drawing, flow amplifier 1 has been adapted for connection with the straight tube 5 by means of interfitting and is covered with insulation material 7.

The flow amplifier 1 is cylindrical and in its interior has a restricted outlet 11 and a diverging frustoconical shape 13 on the downstream side of the restricted inlet 11. On the downstream side of the restricted inlet 11 the amplifier wall contains a plenum chamber 15 within which compressed air is contained after being delivered through line 17 at a controlled pressure determined by control valve 19. A ring nozzle 21 on the interior wall of the flow amplifier having an opening in the range of about 0.002 inch wide represents a restriction to the compressed air in the plenum chamber 15 so that as gas is throttled to atmospheric pressure as it passes through the ring nozzle slot 21, it picks up sonic velocity (1,000 feet/second).

The isokinetic sampling nozzle 3 is attached to the flow amplifier 1 as an extension thereof conveniently having the same external diameter. The leading edge 25 of the isokinetic sampling nozzle is a knife edge formed by cutting back the outer surface of the nozzle to form an angle of 30° between the cut surface 27 and the interior surface of the nozzle 29 forming a vertex at the knife edge 25.

In adapting an isokinetic nozzle for attachment to a commercially produced air flwo amplifier it is necessary to provide a knife edge 25 that is of greater diameter than the internal diameter of the flow amplifier at its furthest point upstream 23. This further requires that the internal diameter of the sampling nozzle be tapered to provide a converging frustoconical shape 9 on the upstream side of the restricted inlet 11 of the flow amplifier. This configuration is necessary to create sample velocity at the inlet of the probe to match the ambient air velocity; that is, to sample isokinetically. The motive air velocity at the ring nozzle 21 of the sample probe is sufficiently higher than the ambient air velocity to provide sufficient pressure to move the sample through the delivery conduit. The converging frustoconical shape 9 provides means by which the relatively slow ambient air velocity can be balanced with the appreciably higher velocity of the motive air so that isokinetic sampling can be achieved.

The straight tube 5 has an interior circumference equal to that of the greatest interior circumference of the discharge side of the flow amplifier and is of sufficient length to allow mixing of motive gas and induced sample before a bend in the delivery tubing is encountered. This is important when drying of the sample is required, but is not a necessary appurtenance for isokinetic sampling of dry gas containing particulate matter. The length required for this operation is dependent upon the sizing of the air flow amplifier.

The apparatus is adaptable for use with any of the gases normally used as motive force in air moving apparatuses. Air and its gaseous components are the most commonly used motive gases for inducing samples from a moist environment. The gases can be used at ambient temperature or, more commonly, will be heated and dried.

It will be evident to those skilled in the art that the dimensions of a sampling probe according to this invention will be dependent upon the size of the air flow amplifier necessary for overcoming back pressure in a specific sampling system. Knowint the pressure that is to be overcome, those skilled in the art can readily calculate the sizing required for the isokinetic sampling nozzle and the straight tube attached to the exit of the air flow amplifier.

The method of this invention will be described in conjunction with the drawing and a specific example of operation. In the drawing a sample probe of this invention is shown connected into motive gas supply and delivery tubing shown by line drawing. Such a system is used in sampling of gas streams before and after filtering devices for removing salt spray. The amount of salt in the sample, as determined by such method as analysis for sodium content, determines the effectiveness of the filterin process. Since the amount of salt is relatively small it is imperative to have the most accurate sampling possible.

For the purpose of illustration a sample probe is constructed using an AM-10 Air Mower by Nortel Machinery Inc. having an inlet internal diameter of 0.394 inches and an outlet internal diameter of 0.75 inches. Attached to the inlet of the air mover is an isokinetic sampling nozzle having an overall length of 1.78 inches, an internal inlet diameter of 0.65 inches, and an internal exit diameter of 0.394 inches. The length of the converging frusto-conical section of the isokinetic sampling nozzle is 0.78 inches. The straight tube attached to the exit of the air mover has an internal diameter of 0.75 inches and the tube is 12 inches in length.

Total backpressure of the illustrative sampling and delivery system was calculated to be 13.4 inches of water column. To overcome this backpressure an AM-10 Air Mover 1 by Nortel Machine;ry Inc. having a motive air consumption of 2.61 cubic feet per minute is required. Total air flow through the Air Mover is the sum of the motive air and sample air (calculated to be 2.61 cubic feet per minute) equal to 5.22 cubic feet per minute.

As the motive air enters the Air Mover periphery 21 at sonic velocity, the sample air at 18.87 feet per second velocity is from this point unable to contact the probe walls. The thin film of sonic velocity motive air follows the contour of the throat venturi wall carrying sample air into the probe. The high velocity thin film of motive air prevents water droplets containing sodium chloride from contactint sample system walls. The sample air is carried by the motive air through the probe drying tube to a mixing point calculated to be 3.5 inches from the throat inlet where it is no longer possible to observe two distinct streams. From that point in the drying tube, through the delivery tube to the analyzer, the sample air and motive air are in a turbulent region and are assumed to be mixed. Calculations have shown that a particle will exchange its water mass to the surrounding dry air in a time of $4.76 \times 10^{-3}$ seconds or about 3.5 inches from the mixing point, for a total distance of 7.0 inches from the inlet throat. Therefore, it can be concluded, as the probe drying tube 5 is 12 inches in length, the sodium particles should be dried before encountering bends in the polyethylene tubing 31.

Motive air is derived from an instrument air system, supplied at 95 psig, a temperature of 65° F. and a minus 40° F. water dew point. The air is filtered (not shown), passes through a regulator 19 and an electrical heater (not shown) to provide motive air at 70 psig and 167.6° F. The motive air is transported through insulated stainless steel tubing 17 to the sample probe Nortel Air Mover 1. Afer entering the Air Mover 1 and mixing with sample air, the resultant blended air has been calculated to be 117° F., based on 65 degree sample air.

At a ratio of 1.0 parts by volume sample air to 1.0 part motive air the sample air is diluted by 50.0 percent and the mixture has a relative humidity of 20 percent. From the probe, the mixed air is pushed through 1.5 inch, insulated polyethylene tubing 31 by the Nortel Air Mover. Flow rates are measured on the sample line discharge, motive air supply line, and air required for analysis. A material balance is calculated to adjust the sample inlet flow rate to obtain isokinetic conditions and the sample dilution ratio. The dilution ratio is necessary to calculate the sodium content of the sample air. Velocity through the delivery tube has been calculated to be 6.6 feet per second. At that rate the mixed air requires about 26 seconds to travel through 175 feet of delivery tubing to an analyzer.

I claim:

1. A sampling probe comprising:

a. a flow amplifier utilizing the Coanda wall attachment effect; and b. attached to the inlet of said flow amplifier a nozzle adapted to induce an isokinetic flow of sample at the operating flow of said amplifier.

2. A sampling probe of claim 1 further comprising a straight tube attached to the outlet of said flow amplifier.

3. A sampling probe of claim 2 for sampling a moist, gaseous environment in which said straight tube is of a length sufficient to allow drying of sampled material.

4. In combination a sampling probe of claim 3 having the flow amplifier connected by transfer means to a source of motive gas.

5. A method for sampling a gaseous environment comprising passing a flow of compressed gas through the throttling inlet of a flow amplifier utilizing the Coanda wall attachment effect thereby inducing flow of sample gas from said gaseous environment through an isokinetic nozzle attached to the inlet of the flow amplifier, through said amplifier and into conveying means attached to the amplifier outlet.

6. A method of claim 5 wherein said isokinetic nozzle is of dimensions to provide an isokinetic flow of sample gas at the operating flow of said amplifier.

7. A method of claim 6 wherein said conveying means comprises a straight tube attached to said amplifier outlet.

8. A method for sampling a moist, gaseous environment comprising the method of claim 6 wherein said compressed gas is at an elevated temperature and dry thereby reducing the moisture content of contacted sample gas.

9. A method for sampling liquid droplets of crystallizable chemical compounds in a moist, gaseous environment comprising the method of claim 6 wherein said straight tube is of length sufficient to produce dry particulate matter in said sample gas.

* * * * *